(12) United States Patent
Benstead

(10) Patent No.: US 10,166,694 B2
(45) Date of Patent: Jan. 1, 2019

(54) RECOVERY OF WOOD ACETYLATION FLUID

(71) Applicant: Tricoya Technologies Ltd, London (GB)

(72) Inventor: Stephen John Benstead, London (GB)

(73) Assignee: Tricoya Technologies Ltd., Windsor (GB)

( * ) Notice: Subject to any disclaimer, the term of this patent is extended or adjusted under 35 U.S.C. 154(b) by 0 days.

(21) Appl. No.: 15/327,027

(22) PCT Filed: Jul. 17, 2015

(86) PCT No.: PCT/EP2015/066436
§ 371 (c)(1),
(2) Date: Jan. 17, 2017

(87) PCT Pub. No.: WO2016/009053
PCT Pub. Date: Jan. 21, 2016

(65) Prior Publication Data
US 2017/0157793 A1    Jun. 8, 2017

(30) Foreign Application Priority Data

Jul. 18, 2014  (GB) .................................. 1412838.3

(51) Int. Cl.
*B27K 3/34* (2006.01)
*B05D 7/06* (2006.01)
(Continued)

(52) U.S. Cl.
CPC .............. *B27K 3/346* (2013.01); *B05D 7/06* (2013.01); *B27K 3/10* (2013.01); *B27K 3/36* (2013.01);
(Continued)

(58) Field of Classification Search
CPC . B27K 3/346; B27K 3/36; B27K 3/10; B27K 2240/70; C07D 51/573; C07D 51/44; C07D 51/56; B05D 7/06; B05D 2203/20
See application file for complete search history.

(56) References Cited

U.S. PATENT DOCUMENTS 8,759,576 B2 * 6/2014 Warner .................... C07C 51/56
562/898
2014/0066653 A1 * 3/2014 Warner ................. C07C 51/573
562/892

(Continued)

FOREIGN PATENT DOCUMENTS

EP      0213252        3/1987
EP      0213252 A1 *   3/1987  ............. B27K 3/346
(Continued)

OTHER PUBLICATIONS

Simonson et al., "A new process for the continuous acetylation of ligoncellulosic fiber," Proceedings of the 5th Pacific Rim Bio-based composites symposium; Dec. 10-13, 2000; Canberra, Australia: Department of Forestry, The Australian National University: 190-196. (Year: 2000).*

*Primary Examiner* — William P Fletcher, III
(74) *Attorney, Agent, or Firm* — OspreyIP, pllc; James R. Cartiglia

(57) ABSTRACT

Disclosed is the integration of the production of acetic anhydride from ketene, and the acetylation of wood using acetylation fluid comprising acetic acid and acetic anhydride. The invention involves recovering acetylation fluid from wood acetylation, and sending this to an acetic anhydride distillation unit belonging to the acetic anhydride production plant.

6 Claims, 2 Drawing Sheets

(51) Int. Cl.
*B27K 3/36* (2006.01)
*B27K 3/10* (2006.01)
*C07C 51/56* (2006.01)
*C07C 51/573* (2006.01)
*C07C 51/44* (2006.01)

(52) U.S. Cl.
CPC .............. *C07C 51/44* (2013.01); *C07C 51/56* (2013.01); *C07C 51/573* (2013.01); *B05D 2203/20* (2013.01); *B27K 2240/70* (2013.01)

(56) References Cited

U.S. PATENT DOCUMENTS

| | | | | |
|---|---|---|---|---|
| 2015/0051423 | A1* | 2/2015 | Amoros | ............... C07C 51/44 562/608 |
| 2016/0229777 | A1* | 8/2016 | Barnicki | ............... C07C 45/48 |
| 2016/0229780 | A1* | 8/2016 | Barnicki | ............... C07C 45/84 |

FOREIGN PATENT DOCUMENTS

| | | | |
|---|---|---|---|
| EP | 0680810 | 11/1995 | |
| EP | 0680810 A1 * | 11/1995 | ............... B27K 1/00 |

\* cited by examiner

RECOVERY OF WOOD ACETYLATION FLUID

FIELD OF THE INVENTION

The invention pertains to a process for the recovery of acetylation fluid from a wood acetylation process. Particularly, the invention pertains to a process wherein the production of acetic anhydride from acetic acid is coupled to a process for the acetylation of wood. Also, the invention relates to an integrated system for the production of acetic anhydride and the acetylation of wood.

BACKGROUND OF THE INVENTION

A well-known process for the production of acetic anhydride from acetic acid involves the formation of ketene (ethenone). Thereby ketene is produced by dehydrating acetic acid at high temperatures (typically in a ketene furnace operated at temperatures of the order of 700° C. to 750° C.). Subsequently, the ketene is reacted with acetic acid in an exothermic reaction leading to the formation of acetic anhydride.

Interestingly, both acetic acid and acetic anhydride are used in processes for the acetylation of wood. These processes, for which there is an increasing demand, serve to provide the wood with improved material properties, e.g. dimensional stability, hardness, durability, etc. In these processes, excess acetylation medium, typically a mixture of acetic anhydride and acetic acid, is ultimately removed from the wood. It is thereby desired to avoid wasting the removed acetylation medium, and preferably to recirculate and re-use it in wood acetylation.

Suitable techniques exist for recovering acetic anhydride, by separating it from acetic acid, after which the acetic anhydride can be re-used in wood acetylation. The acetic acid, however, comes in an excess ratio after wood acetylation as it is formed as a byproduct thereof, and it would be desired to put this to separate use, sell it as a chemical, and/or use it in the production of ketene. However, the specific source of the acetic acid, viz. from the acetylation of wood, comes with inherent limitations to their further use due to the presence impurities such as that of terpenes and terpenoid impurities from the wood. Particularly terpenes and terpenoids are difficult to remove. This limits the use of acetic acid as recovered from wood acetylation. E.g., using it in a ketene furnace is not desired, as the aforementioned impurities are prone to result in coke formation in the furnace, as a result of the high temperatures applied therein.

The foregoing issue is addressed in WO 2009/120257, by azeotropic distillation, wherein acetic acid comprising the aforementioned impurities is supplied to a distillation column together with water. Whilst the reference thus teaches a method of obtaining purified acetic acid from wood acetylation, it does not relate to the production of acetic anhydride and, particularly, it does not teach how to effectively integrate the production of acetic anhydride and the acetylation of wood. Also, the addition of water to the distillation column reduces the economic feasibility of the process. Further, the method would require investment costs and operational costs associated with the addition of a distillation unit.

It is desired to provide a method by which the acetylation of wood and the production of acetic anhydride can be effectively integrated. Also, it is desired to thereby make optimal use of sources of liquid as available from wood acetylation.

SUMMARY OF THE INVENTION

In order to better address one or more of the foregoing desires, the invention, in one aspect, concerns a process for the recovery of acetylation fluid from a wood acetylation process, said fluid comprising acetic acid and acetic anhydride, the process comprising subjecting said fluid to distillation so as to recover acetic acid, wherein the distillation is conducted in an acetic anhydride distillation unit also simultaneously used for distilling off acetic acid from an acetic anhydride product stream obtained in a process for the production of acetic anhydride from ketene and acetic acid.

In another aspect, the invention presents a process for the acetylation of wood, wherein the wood acetylation process is coupled to a process for the production of acetic anhydride, the wood acetylation process comprising subjecting wood to acetylation using an acetylation fluid comprising acetic anhydride and, optionally, acetic acid, and the acetic anhydride production process comprising reacting ketene with acetic acid so as to form an acetic anhydride product stream comprising acetic anhydride and acetic acid, and subjecting said product stream to distillation in an acetic anhydride distillation unit so as to decrease the concentration of acetic acid therein, the process further comprising recovering wood acetylation fluid from the wood acetylation process to obtain recovered acetylation fluid comprising acetic acid and acetic anhydride, and subjecting the recovered acetylation fluid to distillation so as to recover acetic acid, wherein said distillation of recovered acetylation fluid is conducted in the acetic anhydride distillation unit.

In yet another aspect, the invention provides a system comprising a wood acetylation plant and an acetic anhydride production plant, wherein the acetic anhydride production plant comprises a unit for the production of acetic anhydride from ketene and acetic acid and, downstream thereof, an acetic anhydride distillation unit for distilling off acetic acid from a product stream produced in the unit for the production of acetic anhydride, wherein the wood acetylation plant comprises a wood acetylation unit comprising an inlet and an outlet for acetylation fluid, wherein the outlet for acetylation fluid is in fluid communication with an inlet of the acetic anhydride distillation unit.

DETAILED DESCRIPTION OF THE INVENTION

Figure 1:
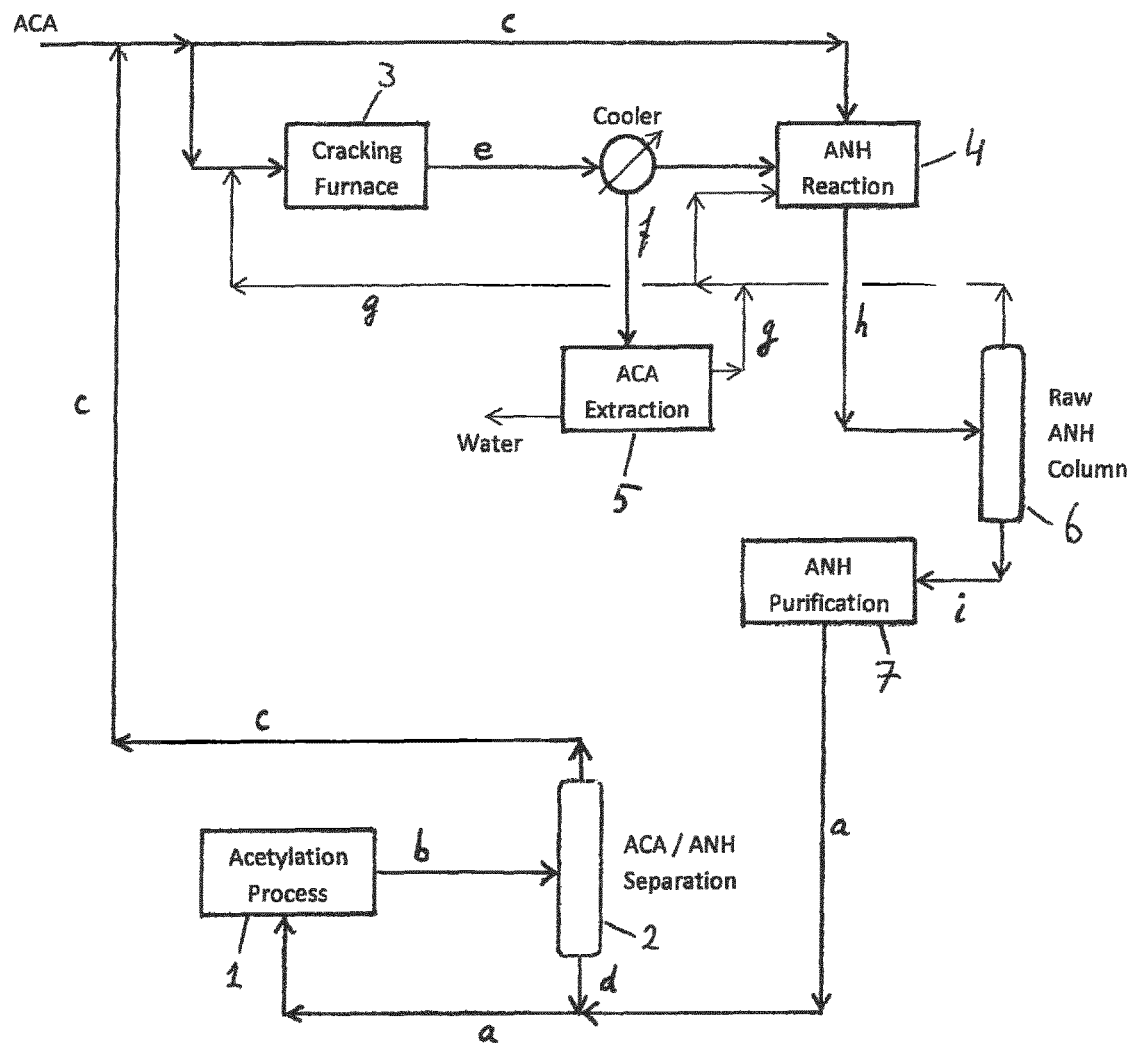
FIG. 1 shows a scheme for a wood acetylation plant coupled to an acetic anhydride production plant without additional measures, not according to the invention.

In a broad sense, the invention is based on the judicious insight to directly send acetylation fluid recovered from wood acetylation, to the step in acetic anhydride production where raw anhydride is distilled, so as to remove acetic acid. Thus, costs are saved by using the anhydride column at the same time also for separation of recovered acetylation fluid.

Additionally, the problem can be circumvented that recovered acetylation fluid is associated with the presence of terpenes, as the invention makes it possible to send acetic acid comprising terpenes and/or terponoids to further treatments not hampered by the presence of these impurities.

This is particularly the case in the event of an interesting embodiment according to which the acetic acid distilled off in the acetic anhydride distillation unit is be mixed with aqueous acetic acid, which is normally obtained as a residual stream from the production of ketene. The production of ketene from acetic acid precedes the synthesis of acetic anhydride from ketene and acetic acid. The residual aqueous acetic acid is normally subject to distillation, so as to recover acetic acid. Since the residual stream is aqueous, the treatment thereof by distillation will allow terpenes and/or terpenoids to be azeotropically removed.

The residual aqueous acetic acid stream results from the fact that, by definition, a unit for the production of ketene from acetic acid (such as a ketene furnace) will not yield a full conversion of acetic acid into ketene. I.e., from said unit at least two streams are obtained. One being a product stream, comprising the formed ketene, the other being said residual stream.

In another interesting embodiment, the acetic anhydride obtained after distillation, is recirculated to the wood acetylation plant, as acetylation fluid. The possible presence of the aforementioned impurities in acetylation fluid does not normally present a problem.

Preferably, the foregoing embodiments are combined so as to yield an integrated process for the acetylation of wood and the production of acetic anhydride. Thereto the invention includes, in a further aspect, a process for the acetylation of wood, wherein the wood acetylation process is coupled to a process for the production of acetic anhydride. The wood acetylation process comprising subjecting wood to acetylation using an acetylation fluid comprising acetic anhydride and, optionally, acetic acid, and the acetic anhydride production process comprising reacting ketene with acetic acid so as to form an acetic anhydride product stream comprising acetic anhydride and acetic acid. Said product stream is subjected to distillation in an acetic anhydride distillation unit so as to decrease the concentration of acetic acid therein. The process further comprises recovering wood acetylation fluid from the wood acetylation process to obtain recovered acetylation fluid comprising acetic acid and acetic anhydride. The recovered acetylation fluid is subjected to distillation so as to recover acetic acid. According to the invention, the distillation of recovered acetylation fluid is conducted in the acetic anhydride distillation unit. Thereby, preferably, the acetic anhydride comprising stream obtained from the acetic anhydride distillation unit, is used as an acetylation fluid in the wood acetylation process.

As the skilled person is aware, the output of the acetic anhydride production unit would normally require adjustment of the ratio of acetic anhydride to acetic acid, so as to become richer in acetic anhydride. This is related to the fact that a full conversion of acetic acid into acetic anhydride will usually not be achieved in practice. A unit for the separation of acetic acid and acetic anhydride (typically a distillation column, sometimes referred to as a "raw anhydride column"), i.e. the aforementioned acetic anhydride distillation unit, its employed in order to adjust the ratio of acetic anhydride to acetic acid in the product stream coming from the acetic anhydride production unit. The output of said separation unit will preferably be suitable for as a wood acetylation fluid, such fluid preferably comprising acetic anhydride (ANH) and acetic acid (ACA) in a ratio ANH:ACA of from 80:20 to 100:0, preferably 90:10 to 95:5.

In the process of the invention, the ketene used in the production of acetic anhydride is produced in a ketene production unit in which acetic acid is heated under ketene forming conditions. Acetic acid distilled off in the acetic anhydride distillation unit is mixed with the aforementioned residual aqueous acetic acid stream from the ketene production unit, and the resulting mixture is subjected to distillation so as to obtain purified acetic acid. The purified acetic acid can be put to any use, but preferably it is used as a reactant for the production of ketene in the ketene production unit.

As a result of the invention, an integrated process is realized wherein wood can be subjected to acetylation, and recovered acetylation fluid is re-used.

The integration of wood acetylation and acetic anhydride production according to the invention can be carried out both in existing plants and in designing new plants. E.g., a new ketene-based production unit for acetic anhydride can be built next to an existing wood acetylation unit, and coupled to it in accordance with one or more embodiments of the invention. Also, a new wood acetylation unit can be built next to an existing ketene-based production unit for acetic anhydride. Or, in the event that a wood acetylation unit and a ketene-based acetic anhydride production unit already exist next to each other, these can become integrated. In the event that the units are already integrated in another way, the manner in which such plants are coupled can be changed so as to be in conformity with the invention as described hereinbefore.

The equipments and technologies applied are well-known to the skilled person. This pertains to units for the acetylation of wood, such as wood acetylation reactors, and the customary ancillary equipment thereof, e.g. a filter section for removing wood residues from recovered acetylation fluid. Similarly, this pertains to distillation units (distillation equipment such as a distillation column), to ketene production sections (typically a ketene furnace), acetic anhydride production sections (typically a reactor suitable for reacting ketene with acetic acid).

Wood acetylation units for use in the present invention can be those suitable for the acetylation of solid wood, such as wood beams or planks. Said wood acetylation units can also be those suitable for the acetylation of wood elements such as flour, fibres, strands, or chips. The wood acetylation processes applied in the present invention thus are not limited to any size, shape, or species of wood. A great variety of such processes is well-known to the skilled person.

The invention also pertains to a system wherein the processes of the invention can be carried out. The system comprises a wood acetylation plant and an acetic anhydride production plant. The acetic anhydride production plant comprises a unit for the production of acetic anhydride from ketene and acetic acid and, downstream thereof, an acetic anhydride distillation unit for distilling off acetic acid from a product stream produced in the unit for the production of acetic anhydride. The wood acetylation plant comprises a wood acetylation unit comprising an inlet and an outlet for acetylation fluid, wherein the outlet for acetylation fluid is in fluid communication with an inlet of the acetic anhydride distillation unit.

Preferably, the acetic anhydride plant also comprises a unit for the production of ketene from acetic acid. This unit (typically a furnace) comprises an inlet for acetic acid and an outlet for produced ketene. The outlet for produced ketene is in fluid communication (typically by means of a gas flow line) with an inlet for the acetic anhydride production unit. The ketene production unit comprises a separate outlet to a section for the treatment of residual aqueous acetic acid.

In a preferred embodiment, the latter treatment section has an inlet in fluid communication with an acetic acid outlet of the acetic anhydride distillation unit. Said distillation unit is positioned downstream of the acetic anhydride production unit and serves, as explained above, for reducing the acetic acid content in the production stream of acetic anhydride originating from the acetic anhydride production unit. According to the invention, the acetic anhydride distillation unit is also fed with acetylation fluid recovered from wood acetylation.

The plants and units referred to above will further have regular ancillary equipment and elements, such as pumps, valves, heaters, and the like. The skilled person will be fully aware of how to build a plant in practice.

The invention will be further explained hereinafter with reference to the drawings. These drawings do not limit the invention. As the drawings may relate to specific embodiments of the invention, the skilled person will understand that the invention is more generally applicable, and the disclosure in the drawings is not limited to any specific designs or numbers given therein.

In the figures, the following elements are shown.
Equipment Parts:
(1) Wood acetylation plant
(2) Acetic acid/acetic anhydride separation unit
(3) Ketene production unit
(4) Acetic anhydride production unit
(5) Treatment section for recovering residual aqueous acetic acid
(6) Acetic anhydride distillation unit
(7) Acetic anhydride purification unit
Process Streams:
(a) Fresh acetylation fluid
(b) Acetylation fluid recovered from wood acetylation
(c) Acetic acid
(d) Acetic anhydride separated from acetic acid
(e) Ketene
(f) Residual aqueous acetic acid
(g) Acetic acid recovered
(h) Raw acetic anhydride (mixture with acetic acid)
(i) Enriched acetic anhydride (reduced acetic acid content)

FIG. 1 shows a scheme for a ketene-based acetic anhydride production plant (comprising a ketene production unit (3) and an acetic anhydride production unit (4) integrated with a wood acetylation plant (1). Herein the plants are coupled without any additional measures, i.e. not according to the invention. Acetylation fluid (stream a) is fed to a wood acetylation plant (1). Recovered acetylation fluid (b) is subjected to acetic acid separation in a first acetic acid/acetic anhydride separation unit (2), resulting in a stream (c) of acetic acid separated from acetic anhydride and a stream (d) of acetic anhydride separated from acetic acid. The stream (c) of acetic acid separated from acetic anhydride is sent to an acetic anhydride production section comprising a ketene production unit (3) and an acetic anhydride production unit (4). The ketene production unit (3) is connected to, downstream thereof, a treatment section (5) for recovering residual aqueous acetic acid (f). Acetic acid recovered therefrom (g) is sent to the ketene production unit (3) and/or the acetic anhydride production unit (4). Ketene produced (e) is sent to an acetic anhydride production unit (4). Raw anhydride produced (h) is sent to an acetic anhydride distillation unit (6). Acetic acid obtained therefrom (c) is sent to the acetic anhydride production section mentioned above. The enriched acetic anhydride (i), having a reduced acetic acid content, is sent to a purification unit (7) and purified acetylation fluid thereby obtained (i) is fed, as fresh acetylation fluid (a) to the wood acetylation section (1).

Figure 2:
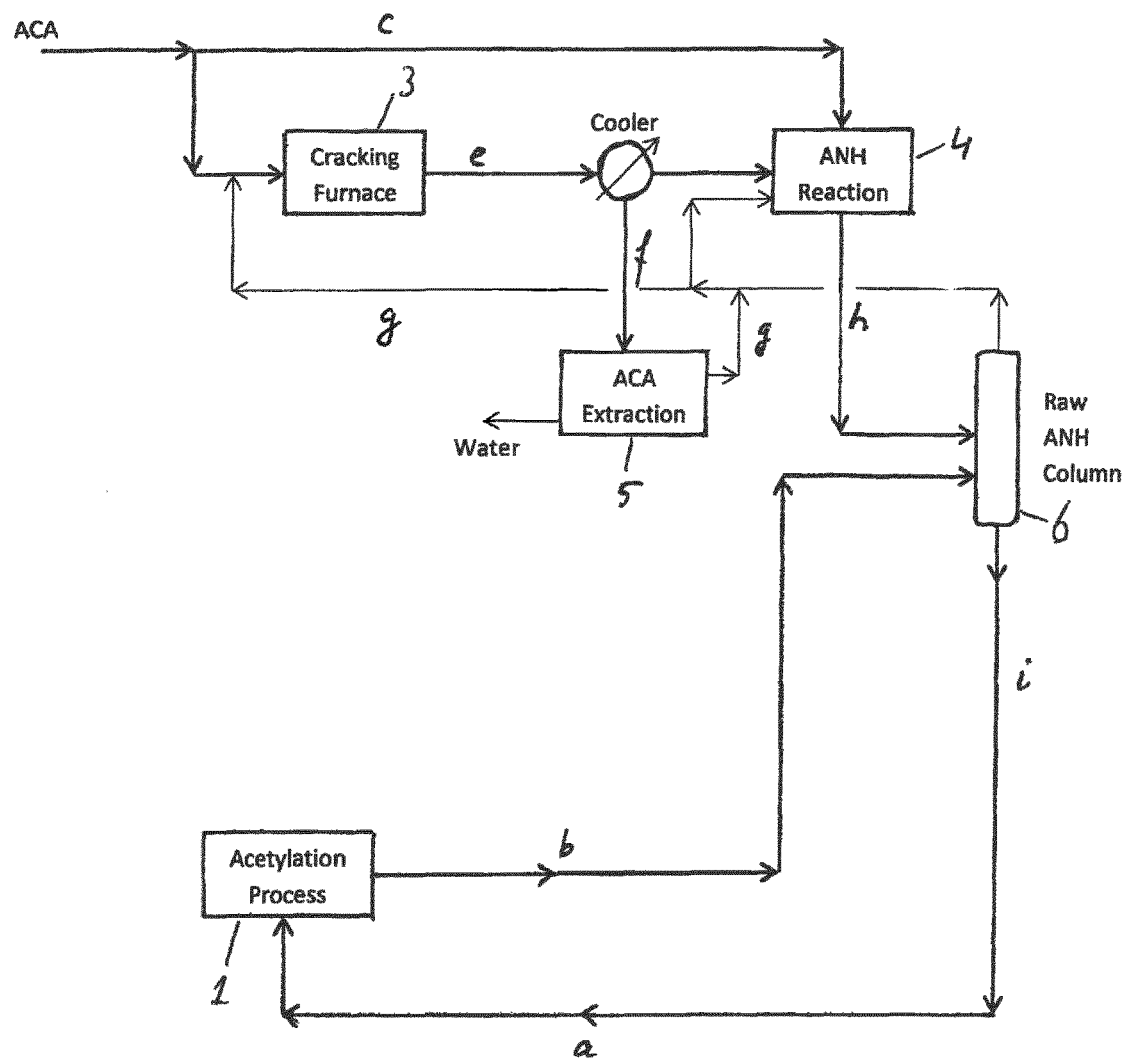
FIG. 2 shows a scheme for a wood acetylation plant coupled to an acetic anhydride production plant according to an embodiment of the invention.

FIG. 2 shows a scheme for a wood acetylation plant coupled to an acetic anhydride production plant in accordance with an embodiment of the invention. Herein the stream (b) of acetylation fluid recovered from the wood acetylation plant (1) acid separated from acetic anhydride is sent to the acetic anhydride distillation unit (6) downstream of the acetic anhydride production unit (4). The original distillation unit (2) downstream of the wood acetylation unit is dispensed with. Further, acetic acid obtained from the acetic anhydride distillation unit (6) can be sent to the treatment section (5) for recovering residual aqueous acetic acid.

It will be understood that the schematic drawings serve to illustrate some parts of the equipments and production units as necessary to further illustrate some embodiments of the invention. The skilled person will be well aware of equipment parts and flow lines now shown, such as devices for providing heat, devices for providing pressure, vents for off-gas, and so on.

Where, in this description, it is spoken of "fluid communication", this refers to any connection between a first part or section of a plant and a second part or section of a plant via which fluids, including liquids and gases, can flow from the first part of the plant to the second part of the plant. In the event of liquids, such fluid communication is typically provided by piping systems, hoses, or other devices well-known to the skilled person for the transportation of fluids. In the event of gases, such fluid communication is typically provided by gas flow lines. Such gas flow lines typically comprise piping systems, or other devices well-known to the skilled person for the transportation of gases, if needed under pressures that are above atmospheric pressures or below (vacuum).

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein described units, such as a wood acetylation unit, a reactor unit or a distillation unit, comprise a plurality of such units positioned in parallel or in series.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

The invention claimed is:

1. A system comprising a wood acetylation plant and an acetic anhydride production plant, wherein the acetic anhydride production plant comprises a unit for the production of acetic anhydride from ketene and acetic acid and, downstream thereof, an acetic anhydride distillation unit for distilling off acetic acid from a product stream produced in the unit for the production of acetic anhydride, wherein the wood acetylation plant comprises a wood acetylation unit comprising an inlet and an outlet for acetylation fluid, wherein the outlet for acetylation fluid is in fluid communication with an inlet of the acetic anhydride distillation unit.

2. A process for the recovery of acetylation fluid from a wood acetylation process, said fluid comprising acetic acid and acetic anhydride, the process comprising subjecting said fluid to distillation so as to recover acetic acid, wherein the distillation is conducted in an acetic anhydride distillation unit also simultaneously used for distilling off acetic acid from an acetic anhydride product stream obtained in a process for the production of acetic anhydride from ketene and acetic acid.

3. A process for the acetylation of wood, wherein the wood acetylation process is coupled to a process for the production of acetic anhydride, the wood acetylation process comprising subjecting wood to acetylation using an acetylation fluid comprising acetic anhydride and, optionally, acetic acid, and the acetic anhydride production process comprising reacting ketene with acetic acid so as to form an acetic anhydride product stream comprising acetic anhydride and acetic acid, and subjecting said product stream to distillation in an acetic anhydride distillation unit so as to decrease the concentration of acetic acid therein, the process further comprising recovering wood acetylation fluid from the wood acetylation process to obtain recovered acetylation fluid comprising acetic acid and acetic anhydride, and subjecting the recovered acetylation fluid to distillation so as to recover acetic acid, wherein said distillation of recovered acetylation fluid is conducted in the acetic anhydride distillation unit.

4. A process according to claim 2 or 3, wherein an acetic anhydride comprising stream obtained from the acetic anhydride distillation unit, is used as an acetylation fluid in the wood acetylation process.

5. A process according to claim 2 or 3, wherein the ketene is produced in a ketene production unit in which acetic acid is heated under ketene forming conditions, and wherein acetic acid distilled off in the acetic anhydride distillation unit is mixed with a residual aqueous acetic acid stream from said ketene production unit, and the resulting mixture is subjected to distillation so as to obtain purified acetic acid.

6. A process according to claim 5, wherein said purified acetic acid is used as a reactant for the production of ketene in the ketene production unit.

* * * * *